United States Patent [19]

Böger et al.

[11] Patent Number: 4,656,183

[45] Date of Patent: Apr. 7, 1987

[54] PESTICIDAL OXALYL DIANILIDES

[75] Inventors: Manfred Böger, Weil am Rhein, Fed. Rep. of Germany; Jozef Drabek, Oberwil; Rainer Neumann, Binningen, both of Switzerland

[73] Assignee: Ciba-Geigy Corporation, Ardsley, N.Y.

[21] Appl. No.: 644,463

[22] Filed: Aug. 27, 1984

[30] Foreign Application Priority Data

Aug. 26, 1983 [CH] Switzerland ............... 4670/83
Mar. 27, 1984 [CH] Switzerland ............... 1525/84

[51] Int. Cl.$^4$ ................ C07D 213/64; A01N 43/40
[52] U.S. Cl. ............................. 514/346; 546/291; 564/155
[58] Field of Search ............ 546/291; 564/155; 514/346

[56] References Cited

U.S. PATENT DOCUMENTS 3,529,982  9/1970  Luethi et al. ............... 427/160

FOREIGN PATENT DOCUMENTS 3135810  4/1982  Fed. Rep. of Germany ...... 564/155
8202447  11/1982  France ..................... 564/155

*Primary Examiner*—Alan L. Rotman
*Attorney, Agent, or Firm*—Edward McC. Roberts; Kevin T. Mansfield

[57] ABSTRACT

The invention relates to novel oxalyl dianilides of the formula

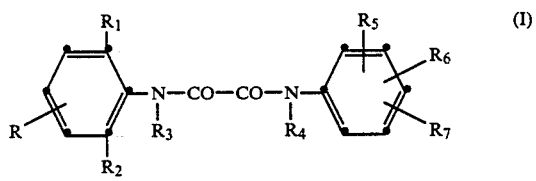

wherein

R is hydrogen, halogen, $C_1$–$C_4$alkyl, methoxy, ethoxy, $C_1$–$C_2$ fluoroalkoxy containing 1 to 5 fluorine atoms, $R_1$ is hydrogen, halogen, methyl, methoxy, ethoxy, $C_1$–$C_2$ fluoroalkoxy containing 1 to 5 fluorine atoms, $C_1$–$C_3$alkylthio or cyano, $R_2$ is hydrogen, halogen, methyl or methoxy, $R_3$ and $R_4$ are each independently hydrogen or methyl, $R_5$ is hydrogen, halogen, methyl, acetyl or trifluoromethyl, $R_6$ is hydrogen, halogen, methyl, trifluoromethyl or carbalkoxy containing 1 to 4 carbon atoms in alkyl moiety, and $R_7$ is hydrogen, $C_1$–$C_3$fluoroalkyl containing 1 to 7 fluorine atoms, $C_1$–$C_3$alkoxy, $C_1$–$C_3$haloalkoxy containing 1 to 7 halogen atoms or is the

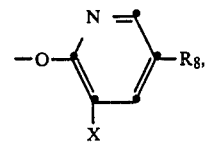

radical, in which $R_8$ is hydrogen, chlorine, trifluoromethyl or a perhalogenated ethyl radical and X is hydrogen or chlorine; or is the

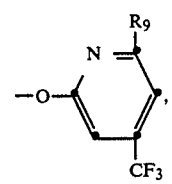

radical, in which $R_9$ is hydrogen, chlorine, bromine, methoxy or ethoxy; or is the

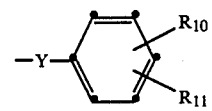

radical, in which $R_{10}$ and $R_{11}$ are each independently hydrogen, halogen, methyl, trifluoromethoxy or trifluoromethyl and Y is an oxygen or a sulfur atom; or is the

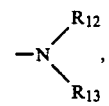

radical, in which $R_{12}$ and $R_{13}$ are $C_1$–$C_5$alkyl, with the proviso that $R_5$, $R_6$ and $R_7$ may not simultaneouly be hydrogen.

The invention also relates to the preparation of these compounds and to compositions containing them for controlling insects and representatives of the order Acarina. The novel compounds have larvicidal activity, in particular against plant destructive insects.

24 Claims, No Drawings

PESTICIDAL OXALYL DIANILIDES

The present invention relates to novel oxalyl dianilides, to the preparation thereof and to their use in pest control.

The compounds of the invention have the formula

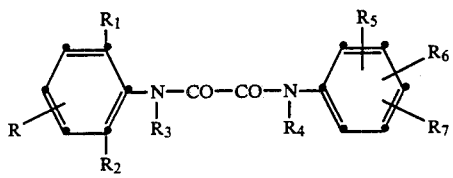 (I)

wherein
R is hydrogen, halogen, $C_1$–$C_4$alkyl, methoxy, ethoxy, $C_1$–$C_2$fluoroalkoxy containing 1 to 5 fluorine atoms,
$R_1$ is hydrogen, halogen, methyl, methoxy, ethoxy, $C_1$–$C_2$fluoroalkoxy containing 1 to 5 fluorine atoms, $C_1$–$C_3$alkylthio or cyano,
$R_2$ is hydrogen, halogen, methyl or methoxy,
$R_3$ and $R_4$ are each independently hydrogen or methyl,
$R_5$ is hydrogen, halogen, methyl, acetyl or trifluoromethyl,
$R_6$ is hydrogen, halogen, methyl, trifluoromethyl or carbalkoxy containing 1 to 4 carbon atoms in the alkyl moiety, and
$R_7$ is hydrogen, $C_1$–$C_3$fluoroalkyl containing 1 to 7 fluorine atoms, $C_1$–$C_3$alkoxy, $C_1$–$C_3$haloalkoxy containing 1 to 7 halogen atoms or is the

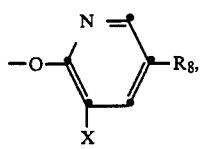

radical, in which $R_8$ is hydrogen, chlorine, trifluoromethyl or a perhalogenated ethyl radical and X is hydrogen or chlorine; or is the

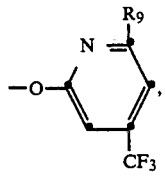

radical, in which $R_9$ is hydrogen, chlorine, bromine, methoxy or ethoxy; or is the

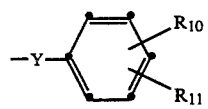

radical, in which $R_{10}$ and $R_{11}$ are each independently hydrogen, halogen, methyl, trifluoromethoxy or trifluoromethyl and Y is an oxygen or a sulfur atom; or is the

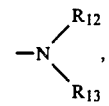

radical, in which $R_{12}$ and $R_{13}$ are $C_1$–$C_5$alkyl,
with the proviso that $R_5$, $R_6$ and $R_7$ may not simultaneously be hydrogen.

Interesting compounds of the formula I are those wherein
R is hydrogen, halogen, $C_1$–$C_4$alkyl, methoxy, ethoxy, $C_1$–$C_2$fluoroalkoxy containing 1 to 5 fluorine atoms,
$R_1$ and $R_2$ are each independently hydrogen, halogen, methyl or methoxy,
$R_3$ and $R_4$ are each independently hydrogen or methyl,
$R_5$ and $R_6$ are each independently hydrogen, halogen, methyl or trifluoromethyl, and
$R_7$ is hydrogen, trifluoromethoxy, fluoroethoxy containing 3 to 5 fluorine atoms, or is the

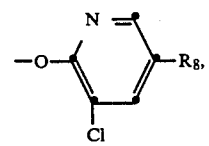

radical, in which $R_8$ is hydrogen, chlorine, trifluoromethyl or a perhalogenated ethyl radical; or is the

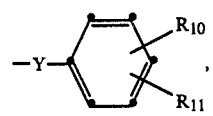

radical, in which $R_{10}$ and $R_{11}$ are each independently hydrogen, halogen, methyl, trifluoromethoxy or trifluoromethyl, and Y is an oxygen or a sulfur atom; or is the

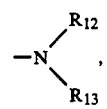

radical, in which $R_{12}$ and $R_{13}$ are $C_1$–$C_5$alkyl.

Other interesting compounds of the formula I are those wherein
R is hydrogen,
$R_1$ is hydrogen, halogen, methyl or methoxy,
$R_2$ is halogen, methyl or methoxy,
$R_3$ and $R_4$ are each independently hydrogen or methyl,
$R_5$ and $R_6$ are each independently hydrogen, halogen, methyl or trifluoromethyl; and
$R_7$ is hydrogen, trifluoromethoxy, the

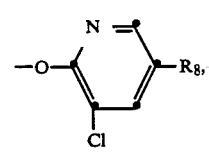

radical, in which $R_8$ is hydrogen, chlorine, trifluoromethyl or a perhalogenated ethyl radical, or the

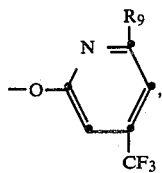

radical, in which $R_9$ is hydrogen, fluorine, chlorine, bromine, methoxy or ethoxy, or the

radical, in which $R_{10}$ and $R_{11}$ are each independently hydrogen, halogen, methyl, trifluoromethoxy or trifluoromethyl, and Y is an oxygen or a sulfur atom, or the

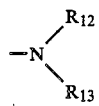

radical, in which $R_{12}$ and $R_{13}$ are $C_1$-$C_5$-alkyl.

Further preferred compounds of the formula I are those wherein
— $R_7$ is in the 4-position on the phenyl ring,
— $R_5$ is hydrogen and $R_7$ is in the 5-position on the phenyl ring,
— $R_6$ is in the 4-position on the phenyl ring,
— $R_5$ and $R_6$ are in the 3- and 5-position respectively on the phenyl ring,
—R is hydrogen;
or also those wherein
$R_1$ is hydrogen, fluorine, chlorine or methoxy,
$R_2$ is hydrogen, fluorine, chlorine, bromine or methoxy,
$R_3$ and $R_4$ are hydrogen,
$R_5$ and $R_6$ are each independently hydrogen, chlorine or methyl,
$R_7$ is trifluoromethoxy, the —O—$CF_2$—$CHF_2$ radical or the

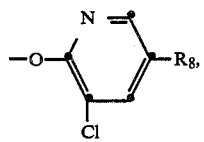

radical, in which $R_8$ is trifluoromethyl or a radical selected from the group consisting of —$CF_2$—$CF_2Cl$, —$CF_2CFCl_2$, —$CCl_2$—$CCl_3$, —$CF_2$—$CCl_3$ or —$CF_2$—$CF_3$, or the

radical, in which $R_{10}$ and $R_{11}$ are each independently hydrogen or chlorine, or the

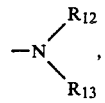

radical, in which $R_{12}$ is methyl and $R_{13}$ is $C_1$-$C_5$alkyl.

On account of their biological activity, particularly interesting compounds of the formula I are those wherein $R_7$ is a radical selected from the group consisting of trifluoromethoxy,

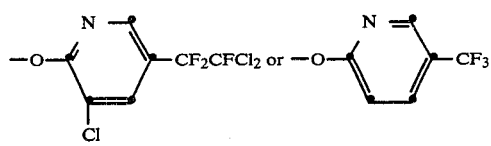

said radical being in the 4-position, or those wherein $R_7$ is a radical selected from the group consisting of —O—$CF_2$—$CHF_2$,

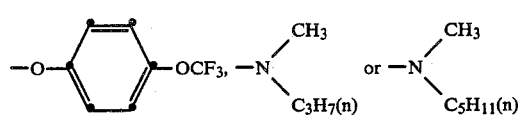

said radical being in the 4-position.

The term "alkyl" will be understood as meaning straight chain and branched alkyl radicals and, depending on the indicated number of carbon atoms, are for example the following groups: methyl, ethyl, propyl, butyl and pentyl, and their isomers, e.g. isopropyl, isobutyl, tert-butyl, isopentyl etc.

Within the scope of this invention, halogen will be taken to mean fluorine, chlorine and bromine, with fluorine and chlorine being the preferred identities.

The compounds of the formula I can be prepared by methods analogous to known ones (q.v. DE-OS 3135810Al). Thus, for example, a compound of the formula I can be obtained by (a) reacting a compound of the formula II

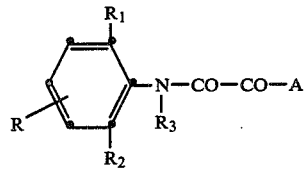

with a compound of the formula III

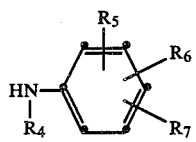

or (b) reacting a compound of the formula IV

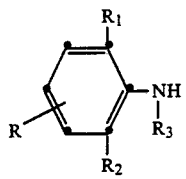

with a compound of the formula V

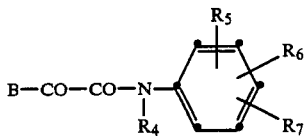

in which formulae II to V above the symbols R to $R_7$ are as defined for formula I, A is methoxy, ethoxy or halogen, preferably chlorine, and B is methoxy or ethoxy.

Processes (a) and (b) above are preferably carried out under normal pressure and by heating or melting the reactants direct, the reaction temperature being in the range from about 40° to 220° C., preferably from 50° to 200° C. However, the reactions can also be carried out in the presence of an inert solvent or diluent having a fairly high boiling point, the reaction temperature being in the range from about 80° to 200° C., preferably at the reflux temperature of the solvent employed. Examples of suitable solvents or diluents are: ethereal compounds such as dibutyl ether, dioxan, dimethoxyethane, and etherified alkylene glycols; N,N-dialkylated carboxamides; aliphatic, aromatic and halogenated hydrocarbons, preferably toluene, a xylene, or chlorobenzene; dimethylsulfoxide and ketones, e.g. methyl isopropyl ketone and methyl isobutyl ketone.

The reaction can be speeded up by the addition of a catalyst, e.g. boric acid. If, for example, an anilidooxalyl chloride of the formula I is used as staring material in process (a), one of the known basic condensing agents will generally be employed, for example a dialkylamine, triethylamine, pyridine, choline and an inorganic base such as sodium carbonate or sodium or potassium bicarbonate.

The starting anilines of the formulae III and IV and the anilidooxalyl derivatives of the formulae II and V are known or can be obtained by methods analogous to known ones. The anilidooxalates of the formulae II and V are obtained e.g. by reacting dialkyl oxalates with the corresponding anilines of the formulae IV and III (q.v. DE-OS 3135810Al).

Anilines of the formula III, wherein $R_7$ is the

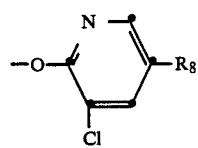

radical or the

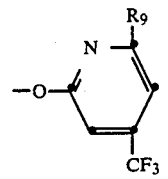

radical, and the preparation thereof, are known from DE-OS 3241138Al and 3240975Al.

Oxalyl dianilides having unsymmetrical substitution with respect to the two phenyl radicals are known from French patent 2 504 915 and DE-OS 3135810Al. The utilities of the compounds described in these publications are for stabilising chlorinated paraffins against heat and UV radiation and for stabilising lacquers and finishes. The compounds of this invention, however, are novel oxalyl dianilides whose structure is characterised in particular by the arrangement of the substituents on the phenyl radicals and which, surprisingly, are very effective pesticides, especially in plant protection. A particular advantage of the compounds of the formula I derives from their very low mammalian toxicity and from the fact that they are well tolerated by plants.

In particular, the compounds of the formula I are suitable for controlling insects of the orders: Lepidoptera, Coleoptera, Homoptera, Heteroptera, Diptera, Thysanoptera, Orthoptera, Anoplura, Siphonaptera, mallophage, Thysanura, Isoptera, Psocoptera and Hymenoptera, as well as representatives of the order Acarina of the families: Ioxididae, Argisidae, Tetranychidae and Dermanyssidae.

In addition to their action against flies, e.g. *Musca domestica*, and mosquito larvae, the compounds of formula I are also suitable for controlling plant-destructive feeding insects in ornamentals and crops of useful plants, especially in cotton (e.g. against *Spodoptera littoralis* and *Heliothis virescens*) and in cereals, fruit and vegetables (e.g. against *Laspeyresia pomonella, Leptinotarsa decemlineata* and *Epilachna varivestis*). The compounds of formula I have a pronounced ovicidal and, in particular, larvicidal action against insects, especially against larvae of noxious feeding insects. If compounds of formula I are ingested by adult insect stages with the feed, then a diminished oviposition and/or reduced hatching rate is observed in many insects, especially in Coleoptera, e.g. *Anthonomus grandis*.

The compounds of formula I can also be used for controlling ectoparasites such as *Lucilia sericata*, in domestic animals and productive livestock, e.g. by treating animals, cowsheds, barns, stables etc., and pastures.

The compounds of formula I are also suitable for controlling the following species of mites which attack crops of fruit and vegetables: *Tetranychus urticae, Tetranychus cinnabarinus, Panonychus ulmi, Broybia rubrioculus, Panonychus citri, Eriophyes piri, Eriophyes ribis, Eriophyes vitis, Tarsonemus pallidus, Phyllocoptes vitis* and *Phyllocoptruta oleivora*.

The good pesticidal activity of the compounds of the formula I corresponds to a mortality of at least 50–60% of the above-mentioned pests.

The activity of the compounds of the formula I and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, pyrethroids, carbamates, chlorinated hydrocarbons, and Bacillus thuringiensis preparations.

The compounds of the formula I are used in unmodified form, or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The formulations, e.g. the compositions or preparations containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers, and in some cases surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi-(2-chloroethyl)-ethylammonium bromide.

The surfactants customarily employed in the art of formulation are described e.g. in "McCutcheon's Detergents and emulsifiers Annual", MC Publishing Corp. Ridgewood, N.J., 1979; Dr. Helmut Stache "Tensid Taschenbuch", Carl Hauser Verlag München/Wien.

The pesticidal compositions usually contain 0.1 to 99%, preferably 0.1 to 95%, of a compound of the formula I or combination thereof with other insecticides or acaricides, 1 to 99.9% of a solid or liquid adjuvant, and 0 to 25%, preferably 0.1 to 25%, of a surfactant.

Whereas commercial products are preferably formulated as concentrates, the end user will normally employ dilute formulations.

The compositions may also contain further ingredients, such as stabilisers, antifoams, viscosity regulators, binders, tackifiers as well as fertilisers or other active ingredients in order to obtain special effects.

FORMULATION EXAMPLES FOR SOLID ACTIVE INGREDIENTS OF THE FORMULA I OR COMBINATIONS THEREOF WITH OTHER INSECTICIDES OR ACARICIDES (THROUGHOUT, PERCENTAGES ARE BY WEIGHT)

| 1. Wettable powders | (a) | (b) | (c) |
|---|---|---|---|
| compound of formula I or combination | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicia acid | 5% | 10% | 10% |
| kaolin | 62% | 27% | — |

The active ingredient or combination is thoroughly mixed with the adjuvants and the mixture is thoroughly ground in a suitable mill, affording wettable powders which can be diluted with water to give suspensions of the desired concentration.

| 2. Emulsifiable concentrate | |
|---|---|
| compound of formula I or combination | 10% |
| octylphenol polyethylene glycol ether (4–5 moles of ethylene oxide) | 3% |
| calcium dodecylbenzesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| 3. Dusts | (a) | (b) |
|---|---|---|
| compound of formula I or combination | 5% | 8% |
| talcum | 95% | — |
| kaolin | — | 92% |

Ready for use dusts are obtained by mixing the active ingredient with the carriers, and grinding the mixture in a suitable mill.

| 4. Extruder granulate | |
|---|---|
| compound of formula I or combinaton | 10% |
| sodium lignosulfonate | 2% |
| carboxymethycellulose | 1% |
| kaolin | 87% |

The active ingredient or combination is mixed and ground with the adjuvants, and the mixture is subsequently moistened with water. The mixture is extruded and then dried in a stream of air.

| 5. Coates granulate | |
|---|---|
| compound of formula I or combination | 3% |
| polyethylene glycol 200 | 3% |
| kaolin | 94% |

The finely ground active ingredient or combination is uniformly applied, in a mixer, to the kaolin moistened with polyethylene glycol. Non-dusty coated granulates are obtained in this manner.

| 6. Suspension concentrate | |
|---|---|
| compound of formula I or combination | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient or combination is intimately mixed with the adjuvants, giving a suspension concentrate from which suspensions of any desired concentration can be obtained by dilution with water.

EXAMPLE 1

Preparation of N-(2,6-difluorophenyl)-N'-[4-(3-chloro-5-trifluoromethyl-2-pyridyloxy)-3,5-dichlorophenyl]oxalyl dianilide: With stirring, 8.9 g of 3-chloro-5-trifluoromethyl-2-pyridyl-2,6-dichloro-4-aminophenyl ether, 5.4 g of methyl 2,6-difluorophenylaminoooxoacetate and 20 ml of chlorobenzene are heated for 3 hours to the boil (bath temperature about 150° C.). After the reaction mixture has cooled, hexane is added and the precipitate is filtered with suction and washed with hexane. Recrystallisation from toluene yields the title compound of the formula

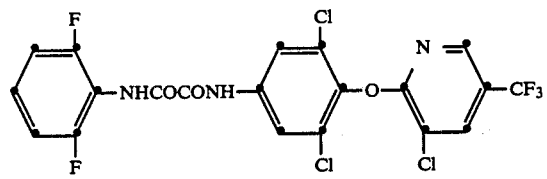

as a white crystalline solid with a melting point of 202°–203° C. (compound 1).

The following compounds of formula I are prepared in analogous manner:

| Compound No. | | m.p. [°C.] |
|---|---|---|
| 2 | 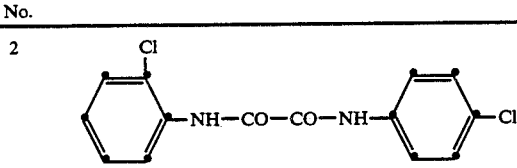 | 212–213 |

-continued
| Compound No. | Structure | m.p. [°C] |
|---|---|---|
| 3 | 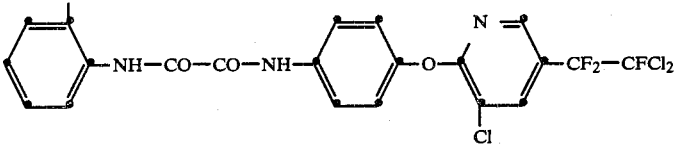 | 174–176 |
| 4 | 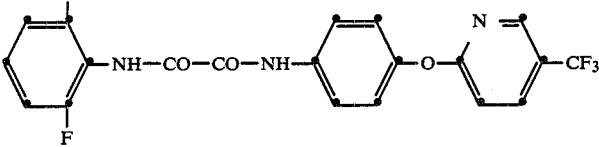 | 209–211 |
| 5 | 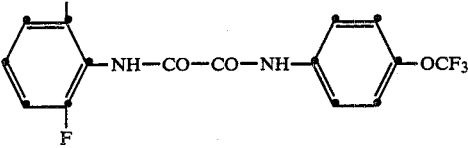 | 203–205 |
| 6 | 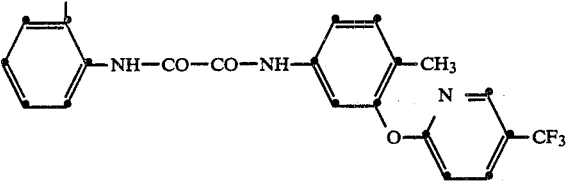 | 177–179 |
| 7 | 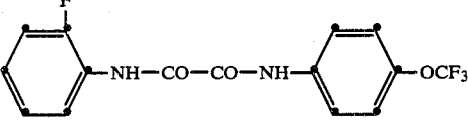 | 183–185 |
| 8 | 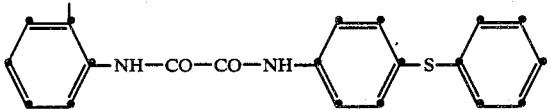 | 166–168 |
| 9 | 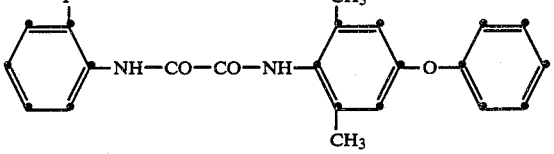 | 144–146 |
| 10 | 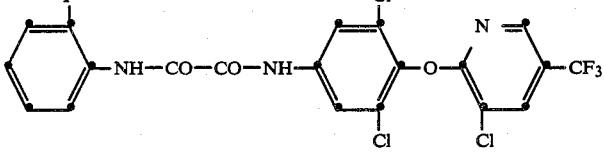 | 165–167 |
| 11 | 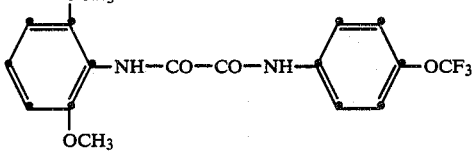 | 186–188 |

-continued

| Compound No. | Structure | m.p. [°C] |
|---|---|---|
| 12 | 2,6-(OCH$_3$)$_2$-C$_6$H$_3$-NH-CO-CO-NH-C$_6$H$_4$-O-[3-Cl-5-(CF$_2$CFCl$_2$)-pyridin-2-yl] | 204–206 |
| 13 | 2-F-C$_6$H$_4$-NH-CO-CO-NH-[3,5-Cl$_2$-4-(N(CH$_3$)(n-C$_5$H$_{11}$))-C$_6$H$_2$] | 74–76 |
| 14 | 2,6-(CH$_3$)$_2$-C$_6$H$_3$-NH-CO-CO-NH-[3,5-Cl$_2$-4-O-(3-Cl-5-CF$_3$-pyridin-2-yl)-C$_6$H$_2$] | 163–165 |
| 15 | 2-F-C$_6$H$_4$-NH-CO-CO-NH-(2-CF$_3$-C$_6$H$_4$) | 140–142 |
| 16 | 2-F-C$_6$H$_4$-NH-CO-CO-NH-C$_6$H$_4$-O-C$_6$H$_4$-4-CF$_3$ | 137–140 |
| 17 | 2,6-Cl$_2$-C$_6$H$_3$-NH-CO-CO-NH-C$_6$H$_4$-4-OCF$_3$ | 211–212 |
| 18 | 2-Br-C$_6$H$_4$-NH-CO-CO-NH-[3,5-Cl$_2$-4-O-(3-Cl-5-CF$_3$-pyridin-2-yl)-C$_6$H$_2$] | 155–157 |
| 19 | 2-Br-C$_6$H$_4$-NH-CO-CO-NH-C$_6$H$_4$-S-C$_6$H$_4$-4-CH$_3$ | 167–169 |
| 20 | 2,6-(OCH$_3$)$_2$-C$_6$H$_3$-NH-CO-CO-NH-[3,5-Cl$_2$-4-O-(3-Cl-5-CF$_3$-pyridin-2-yl)-C$_6$H$_2$] | 205–207 |

-continued

| Compound No. | Structure | m.p. [°C.] |
|---|---|---|
| 21 | 2-Br-C₆H₄-NH-CO-CO-NH-C₆H₄-4-OCF₃ | 172–173 |
| 22 | 2,6-Cl₂-C₆H₃-NH-CO-CO-NH-C₆H₄-4-O-C₆H₅ | 202–204 |
| 23 | 2-CH₃-6-Cl-C₆H₃-NH-CO-CO-NH-(2,6-Cl₂-C₆H₂-4-O-(3-Cl-5-CF₃-pyridin-2-yl)) | 197–199 |
| 24 | 2,6-Cl₂-C₆H₃-NH-CO-CO-NH-(2,6-Cl₂-C₆H₂-4-O-(3-Cl-5-CF₃-pyridin-2-yl)) | 225–227 |
| 25 | 2-Cl-C₆H₄-NH-CO-CO-NH-C₆H₄-4-S-C₆H₅ | 174–175 |
| 26 | 2-F-C₆H₄-NH-CO-CO-NH-C₆H₄-4-S-C₆H₄-4-Cl | 169–170 |
| 27 | 2-CH₃-C₆H₄-NH-CO-CO-NH-(2,6-Cl₂-C₆H₂-4-O-(3-Cl-5-CF₃-pyridin-2-yl)) | 139–141 |
| 28 | 2-F-C₆H₄-NH-CO-CO-NH-(2-Cl-C₆H₃-4-O-(3-Cl-5-CF₃-pyridin-2-yl)) | 162–164 |
| 29 | 2-OCH₃-C₆H₄-NH-CO-CO-NH-C₆H₄-4-S-C₆H₅ | 139–141 |

-continued

| Compound No. | Structure | m.p. [°C.] |
|---|---|---|
| 30 | 2-Br-C₆H₄-NH-CO-CO-NH-C₆H₄-S-C₆H₅ | 169–171 |
| 31 | 2-F-C₆H₄-NH-CO-CO-NH-C₆H₄-O-C₆H₅ | 174–176 |
| 32 | 2-OCH₃-C₆H₄-NH-CO-CO-NH-(2,6-diCl-C₆H₂)-O-(3-Cl-5-CF₃-pyridin-2-yl) | 141–144 |
| 33 | 2-F-C₆H₄-NH-CO-CO-NH-C₆H₄-O-(3-Cl-5-(CF₂-CFCl₂)-pyridin-2-yl) | 206–208 |
| 34 | 2-F-C₆H₄-NH-CO-CO-NH-(2-Br-C₆H₃)-O-(3-Cl-5-CF₃-pyridin-2-yl) | 188–190 |
| 35 | 2-F-C₆H₄-NH-CO-CO-NH-(2-CH₃-C₆H₃)-O-(3-Cl-5-CF₃-pyridin-2-yl) | 157–159 |
| 36 | 2-F-C₆H₄-NH-CO-CO-NH-(2-Cl-C₆H₃)-O-(3-Cl-5-CF₃-pyridin-2-yl) | 173–175 |
| 37 | 2-Cl-C₆H₄-NH-CO-CO-NH-(2,6-diCl-C₆H₂)-O-(3-Cl-5-CF₃-pyridin-2-yl) | 157–159 |

-continued

| Compound No. | Structure | m.p. [°C.] |
|---|---|---|
| 38 | 2-F-C6H4-NH-CO-CO-NH-C6H3(2-CH3)-O-(pyridyl: 3-Cl, 5-CF3) | 167–169 |
| 39 | C6H5-NH-CO-CO-NH-C6H2(2,6-Cl2)-O-(pyridyl: 3-Cl, 5-CF3) | 203–205 |
| 40 | 2-CN-C6H4-NH-CO-CO-NH-C6H2(2,6-Cl2)-O-(pyridyl: 3-Cl, 5-CF3) | 247–248 |
| 41 | 2-F-C6H4-NH-CO-CO-NH-C6H2(2,6-Cl2)-O-(pyridyl: 3-Cl, 5-CF3) | 181–182 |
| 42 | 4-F-C6H4-NH-CO-CO-NH-C6H2(2,6-Cl2)-O-(pyridyl: 3-Cl, 5-CF3) | 179–181 |
| 43 | 2-OC2H5-C6H4-NH-CO-CO-NH-C6H2(2,6-Cl2)-O-(pyridyl: 3-Cl, 5-CF3) | 91–93 |
| 44 | 2-F-C6H4-NH-CO-CO-NH-C6H2(2,6-Cl2)-O-CF2-CHF2 | 147–149 |
| 45 | 2,4-Cl2-C6H3-NH-CO-CO-NH-C6H2(2,6-Cl2)-O-(pyridyl: 3-Cl, 5-CF3) | 191–193 |
| 46 | 2-OC2F5-C6H4-NH-CO-CO-NH-C6H2(2,6-Cl2)-O-(pyridyl: 3-Cl, 5-CF3) | 177–179 |

-continued

| Compound No. | Structure | m.p. [°C.] |
|---|---|---|
| 47 | 2-CN-C₆H₄-NH-CO-CO-NH-C₆H₄-4-O-CF₃ | 242-244 |
| 48 | 4-(CHF₂O)-C₆H₄-NH-CO-CO-NH-(3,5-Cl₂-4-(5-CF₃-3-Cl-pyridin-2-yloxy)phenyl) | 177-180 |
| 49 | 3-(O-CF₂CHF₂)-C₆H₄-NH-CO-CO-NH-(3,5-Cl₂-4-(5-CF₃-3-Cl-pyridin-2-yloxy)phenyl) | 146-148 |
| 50 | 2-(S-(CH₂)₂-CH₃)-C₆H₄-NH-CO-CO-NH-(3,5-Cl₂-4-(5-CF₃-3-Cl-pyridin-2-yloxy)phenyl) | 208-210 |
| 51 | 4-(CHF₂CF₂-O)-C₆H₄-NH-CO-CO-NH-(3,5-Cl₂-4-(5-CF₃-3-Cl-pyridin-2-yloxy)phenyl) | 233-235 |
| 52 | 2-F-C₆H₄-NH-CO-CO-NH-(5-(CO-OCH₃)-2-(5-CF₃-3-Cl-pyridin-2-yloxy)phenyl) | 205-208 |
| 53 | 4-C₂H₅-C₆H₄-NH-CO-CO-NH-(3,5-Cl₂-4-(5-CF₃-3-Cl-pyridin-2-yloxy)phenyl) | 203-205 |
| 54 | 2-C₂H₅-C₆H₄-NH-CO-CO-NH-(3,5-Cl₂-4-(5-CF₃-3-Cl-pyridin-2-yloxy)phenyl) | 150-152 |
| 55 | 2-(O-CH₂CF₃)-C₆H₄-NH-CO-CO-NH-(3,5-Cl₂-4-(5-CF₃-3-Cl-pyridin-2-yloxy)phenyl) | 210-212 |

-continued

| Compound No. | Structure | m.p. [°C] |
|---|---|---|
| 56 | (CH₃)₃C—C₆H₄—NH—CO—CO—NH—C₆H₂(Cl)(Cl)—O—C₅HN(Cl)(CF₃) | 160 |
| 57 | C₆H₅—NH—CO—CO—NH—C₆H₂(Cl)(Cl)—O—C₅H₂N(CF₃) | 202–204 |
| 58 | CH₃—C₆H₄—NH—CO—CO—NH—C₆H₂(Cl)(Cl)—O—C₅HN(Cl)(CF₃) | 213–215 |
| 59 | C₆H₅—NH—CO—CO—NH—C₆H₄—O—CF₃ | 217–219 |
| 60 | Cl—C₆H₄—NH—CO—CO—NH—C₆H₄—O—CF₃ | 229–231 |
| 61 | Cl—C₆H₄—NH—CO—CO—NH—C₆H₂(Cl)(Cl)—O—CF₂CHF₂ | 208–210 |
| 62 | C₆H₅—NH—CO—CO—NH—C₆H₂(Cl)(Cl)—O—CF₂CHF₂ | 176–178 |
| 63 | F—C₆H₄—NH—CO—CO—NH—C₆H₂(Cl)(Cl)—O—CF₂CHF₂ | 182–184 |
| 64 | C₆H₅—NH—CO—CO—NH—C₆H₃(CO—OCH₃)—O—C₅HN(Cl)(CF₃) | 252–254 |

| Compound No. | Structure | m.p. [°C] |
|---|---|---|
| 65 | 4-Cl-C6H4-NH-CO-CO-NH-(2,6-diCl-4-yl)-O-(3-Cl-5-CF3-pyridin-2-yl) | 218–220 |
| 66 | C6H5-NH-CO-CO-NH-(3-CH3-4-yl)-O-(3-Cl-5-CF3-pyridin-2-yl) | 214–216 |
| 67 | 4-F-C6H4-NH-CO-CO-NH-(2,6-diCl-4-yl)-O-(5-CF3-pyridin-2-yl) | 213–215 |
| 68 | 4-(CH3)3C-C6H4-NH-CO-CO-N(CH3)-(3,4-diCl-C6H3) | 91–94 |
| 69 | C6H5-N(CH3)-CO-CO-NH-(3,5-diCl-4-OCF2CHF2-C6H2) | 138–140 |
| 70 | C6H5-N(CH3)-CO-CO-NH-(2,6-diCl-4-yl)-O-(3-Cl-5-CF3-pyridin-2-yl) | 160–162° C. |

The following compounds of formula I can also be prepared in corresponding manner:

| Compound No. | Structure |
|---|---|
| 71 | 2,6-diF-C6H3-NH-CO-CO-N(CH3)-(3-CH3-4-yl)-O-(3-Cl-5-CF3-pyridin-2-yl) |
| 72 | 2-Cl-C6H4-N(CH3)-CO-CO-NH-(4-OCF3-C6H4) |

| Compound No. | |
|---|---|
| 73 | 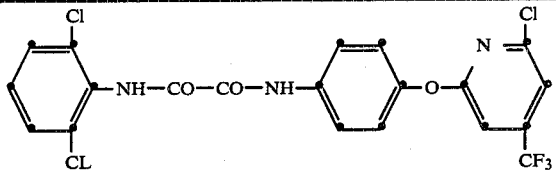 |

EXAMPLE 2

Action against *Musca domestica*

50 g of freshly prepared nutrient substrate for maggots are charged into each of a number of beakers. A specific amount of a 1% acetonic solution of the respective test compound is pipetted onto the nutrient substrate present in the beakers to give an active ingredient concentration of 400 ppm. The substrate is then thoroughly mixed and the acetone subsequently allowed to evaporate over a period of at least 20 hours.

Then 25 one-day-old maggots of *Musca domestica* are put into each of the beakers containing the treated nutrient substrate for testing with each active ingredient at one of its given concentrations. After the maggots have pupated, the pupae are separated from the substrate by flushing them out with water and then deposited in containers closed with a perforated top.

Each batch of flushed out pupae is counted to determine the toxic effect of the test compound on the maggot development. A count is then made after 10 days of the number of flies which have hatched out of the pupae.

The compounds of formula I obtained according to Example 1 have good activity in this test.

EXAMPLE 3

Action against *Lucilia sericata*

1 ml of an aqueous solution containing 0.5% of test compound is added at 50° C. to 9 ml of a culture medium. Then about 30 freshly hatched *Lucilia sericata* larvae are added to the culture medium, and the insecticidal action is determined after 48 and 96 hours by evaluating the mortality rate. In this test, compounds of the formula I according to Example 1 exhibit good activity against *Lucilia sericata*.

EXAMPLE 4

Action against *Aedes aegypti*

A concentration of 800 ppm is obtained by pipetting a specific amount of a 0.1% solution of the test compound in acetone onto the surface of 150 ml of water in a beaker. After the acetone has evaporated, 30 to 40 two-day-old larvae of *Aedes aegypti* are put into the beaker containing the solution of the test compound. Mortality counts are made after 1, 2 and 5 days.

In this test, compounds of Example 1 exhibit good activity against *Aedes aegypti*.

EXAMPLE 5

Insecticidal action against feeding insects

Cotton plants about 25 cm high, in pots, are sprayed with aqueous emulsions which contain the test compound in concentrations of 400, 200, 50, 12.5 and 3.0 ppm. After the spray coating has dried, the cotton plants are populated with *Spodoptera littoralis* and *Heliothis virescens* larvae in the $L_3$-stage. The test is carried out at 24° C. and 60% relative humidity. The percentage mortality of the test insects is determined after 120 hours.

EXAMPLE 6

Action against *Epilchna varivestis*

*Phaseolus vulgaris* plants (dwarf beans) about 15-20 cm in height are sprayed with aqueous emulsion formulations of the test compound in concentrations of 800 ppm. After the spray coating has dried, each plant is populated with 5 larvae of *Epilachna varivestis* (Mexican bean beetle) in the $L_4$-stage. A plastic cylinder is slipped over the treated plants and covered with a copper gauze top. The test is carried out at 28° C. and 60% relative humidity. The percentage mortality is determined after 2 and 3 days. Evaluation of feeding damage (anti-feeding effect), and of inhibition of development and shedding, is made by observing the test insects for a further 3 days.

The compounds of Example 1 exhibit good activity in this test.

EXAMPLE 7

Ovicidal action against *Heliothis virescens*

Corresponding amounts of a wettable powder formulation containing 25% by weight of the test compound are mixed with sufficient water to produce an aqueous emulsion with an active ingredient concentration of 800 ppm. One day-old egg deposits of Heliothis on cellophane are immersed in these emulsions for 3 minutes and then collected by suction on round filters. The treated deposits are placed in petri dishes and kept in the dark. The hatching rate in comparison with untreated controls is determined after 6 to 8 days. Evaluation is made by determining the minimum concentration necessary for 100% kill of the eggs.

In this test the compounds of Example 1 exhibit good ovicidal action.

EXAMPLE 8

Action against *Laspeyresia pomonella* (eggs)

Egg deposits of *Laspeyrasia pomonella* not more than 24 hours old are immersed on filter paper for 1 minute in an acetonic solution containing 800 ppm of the test compound.

After the solution has dried, the eggs are placed in petri dishes and kept at a temperature of 28° C. The percentage of larvae hatched from the treated eggs and the percentage mortality is evaluated after 6 days. The compounds of formula I according to Example 1 exhibit good activity in this test.

EXAMPLE 9

Influence on th reprduction of *Anthonomous grandis*

*Anthonomous grandis* adults which are not more than 24 hours old after hatching are transferred in groups of 25 to barred cages. The cages are then immersed for 5 to 10 seconds in an acetonic solution containing 1.0% by weight of the test compond. After the beetles have dried, they are placed in covered dishes containing feed and left for copulation and oviposition. Egg deposits are flushed out with running water twice to three times weekly, counted, disinfected by putting them for 2 to 3 hours into an aqueous disinfectant, and then placed in dishes containing a suitable larval feed. A count is made after 7 days to determine whether larvae have developed from the eggs.

The duration of the reproduction inhibiting effect of the test compounds is determined by monitoring the egg deposits over a period of about 4 weeks. Evaluation is made by assessing the reduction in the number of deposited eggs and hatched larvae in comparison with untreated controls.

The compounds of the formula I exhibit a good reproduction inhibiting effect in this test.

EXAMPLE 10

Acaricidal action 12 hours before the test for acaricidal action, *Phaseolus vulgaris* plants are infected with an infested piece of leaf from a mass culture of *Tetranychus urticae*. The treated plants infested with the mobile stages which have migrated to the plants are sprayed dripping wet from a chromatography atomiser with emulsified test solutions each having an active ingredient concentration of 800 ppm. A count of living and dead adults and larvae is made under a stereoscopic microscope after 2 days and again after 7 days. The result is expressed in percent. During the test run, the plants stand in greenhouse compartments at 25° C.

Compounds of the formula I according to Example 1 exhibit good activity in the above test.

EXAMPLE 11

Action against *Anthonomus grandis* (adults)

Two cotton plants in the 6-leaf stage, in pots, are each sprayed with a wettable aqueous emulsion formulation containing the test compound in a concentration of 50 and 200 ppm. After the spray coating has dried (about 1½ hours), each plant is populated with 10 adult beetles (*Anthonomus grandis*). Plastic cylinders, covered at the top with gauze, are then slipped over the treated plants populated with the test insects to prevent the beetles from migrating from the plants. The treated plants are then kept at 25° C. and about 60% relative humidity. Evaluation is made after 2, 3, 4 and 5 days to determine the perecentage mortality of the beetles (dorsal position) as well as the anti-feeding action as compared with untreated controls.

RESULTS OF THE BIOLOGICAL TESTS

The results of the biological tests carried out with the compounds of the invention in accordance with the foregoing Examples are reported in the following table. Evaluation of the tests in terms of percentage mortality is made using the following rating:

A: 80–100% mortality at a concentration of 3.0 ppm of the tested compound
B: 80–100% mortality at a concentration of 12.5 ppm of the tested compound
C: 80–100% mortality at a concentration of 50 ppm of the tested compound
D: 80–100% mortality at a concentration of 100 ppm of the tested compound
E: 80–100% mortality at a concentration of 200 ppm of the tested compound
F: 80–100% mortality at a concentration of 400 ppm of the tested compound
—: not tested.

| Compound No. | Pesticidal activity | | |
|---|---|---|---|
| | Spodoptera (Example 5) | Heliothis (Example 5) | Anthonomus (Example 11) |
| 1 | B | C | E |
| 4 | F | — | C |
| 10 | A | B | C |
| 13 | F | — | — |
| 17 | F | — | — |
| 18 | C | — | — |
| 20 | E | — | — |
| 23 | F | — | — |
| 24 | F | — | — |
| 27 | C | D | E |
| 28 | C | F | F |
| 32 | F | — | — |
| 35 | F | — | — |
| 39 | A | E | — |
| 40 | D | — | — |
| 41 | F | — | — |
| 42 | B | F | — |
| 43 | F | — | — |
| 44 | F | — | — |
| 45 | F | — | — |

What is claimed is:
1. A compound of the formula

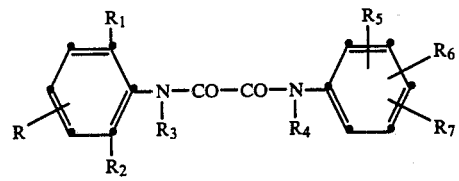

wherein
R is hydrogen, halogen, $C_1$–$C_4$alkyl, methoxy, ethoxy, $C_1$–$C_2$fluoroalkoxy containing 1 to 5 fluorine atoms,
$R_1$ is hydrogen, halogen, methyl, methoxy, ethoxy, $C_1$–$C_2$fluoroalkoxy containing 1 to 5 fluorine atoms, $C_1$–$C_3$alkylthio or cyano,
$R_2$ is hydrogen, halogen, methyl or methoxy,
$R_3$ and $R_4$ are each independently hydrogen or methyl,
$R_5$ is hydrogen, halogen, methyl, acetyl or trifluoromethyl,
$R_6$ is hydrogen, halogen, methyl, trifluoromethyl or carbalkoxy containing 1 to 4 carbon atoms in the alkyl moiety, and
$R_7$ is the

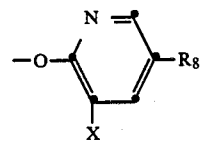

radical, in which R$_8$ is hydrogen, chlorine, trifluoromethyl or a perhalogenated ethyl radical and X is hydrogen or chlorine; or is the

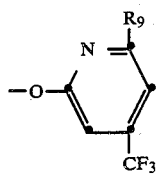

radical, in which R$_9$ is hydrogen, chlorine, bromine, methoxy or ethoxy.

2. A compound according to claim 1, wherein
R is hydrogen, halogen, C$_1$–C$_4$alkyl, methoxy, ethoxy, C$_1$–C$_2$fluoroalkoxy containing 1 to 5 fluorine atoms,
R$_1$ and R$_2$ are each independently hydrogen, halogen, methyl or methoxy,
R$_3$ and R$_4$ are each independently hydrogen or methyl,
R$_5$ and R$_6$ are each independently hydrogen, halogen, methyl or trifluoromethyl, and
R$_7$ fluorine is the

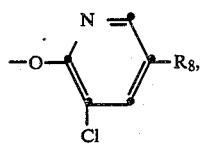

radical, in which R$_8$ is hydrogen, chlorine, trifluoromethyl or a perhalogenated ethyl radical.

3. A compound according to claim 1, wherein
R is hydrogen,
R$_1$ is hydrogen, halogen, methyl or methoxy,
R$_2$ is halogen, methyl or methoxy,
R$_3$ and R$_4$ are each independently hydrogen or methyl,
R$_5$ and R$_6$ are each independently hydrogen, halogen, methyl or trifluoromethyl; and
R$_7$ is the

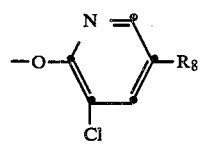

radical in which R$_8$ is hydrogen, chlorine, trifluoromethyl or a perhalogenated ethyl radical, or the

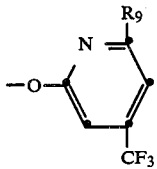

radical, in which R$_9$ is hydrogen, fluorine, chlorine, bromine, methoxy or ethoxy.

4. A compound according to claims 1 to 3, wherein R$_7$ is in the 4-position on the phenyl ring.

5. A compound according to claims 1 to 3, wherein R$_5$ is hydrogen and R$_7$ is in the 5-position on the phenyl ring.

6. A compound according to claim 5, wherein R$_6$ is in the 4-position on the phenyl ring.

7. A compound according to claims 1, 2 or 3, wherein R$_5$ and R$_6$ are in the 3- and 5-position respectively on the phenyl ring.

8. A compound of claims 1 or 2, wherein R is hydrogen.

9. A compound according to claims 1 or 2, wherein
R$_1$ is hydrogen, fluorine, chlorine or methoxy,
R$_2$ is hydrogen, fluorine, chlorine, bromine or methoxy,
R$_3$ and R$_4$ are hydrogen,
R$_5$ and R$_6$ are each independently hydrogen, chlorine or methyl,
R$_7$ is the

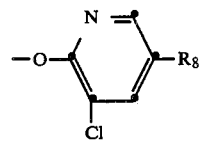

radical, in which R$_8$ is trifluoromethyl or a radical selected from the group consisting of —CF$_2$—CF$_2$Cl, —CF$_2$CFCl$_2$, —CCl$_2$—CCl$_3$, —CF$_2$—CCl$_3$ or —CF$_2$—CF$_3$.

10. A compound according to claims 1, 2 or 3, wherein R$_7$ is a radical selected from the group consisting of,

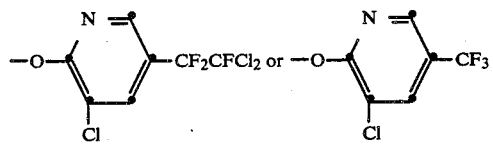

said radical being in the 4-position.

11. A compound according to claim 1, wherein R$_7$ is the radical

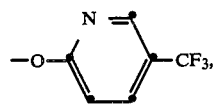

said radical being in the 4-position.

12. A compound according to claim 10 of the formula

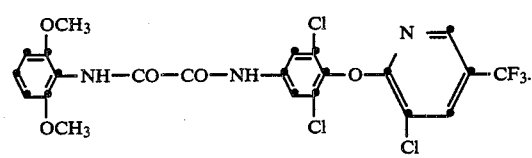

13. A compound according to claim 10 of the formula

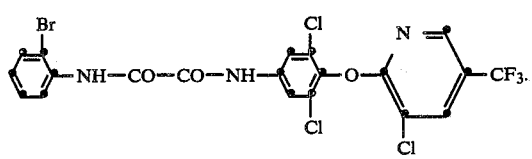

14. A compound according to claim 10 of the formula

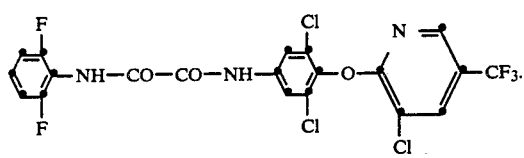

15. A compound according to claim 11 of the formula

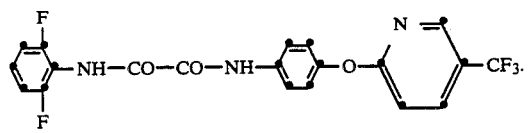

16. A compound of claim 5 of the formula

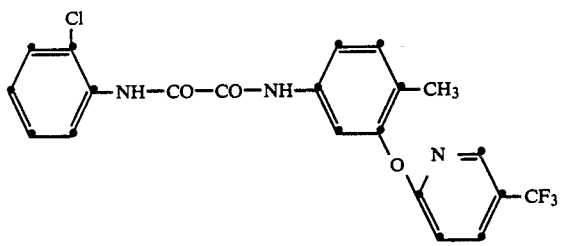

17. A compound according to claim 10 of the formula

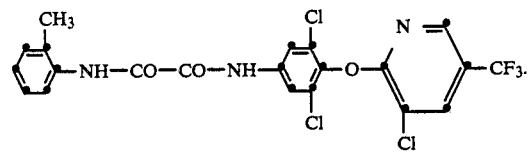

18. A compound according to claim 1 of the formula

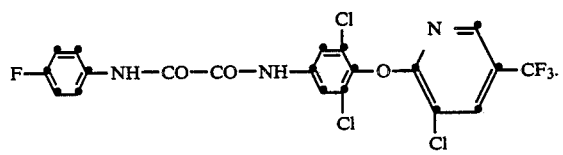

19. A compound according to claim 10 of the formula

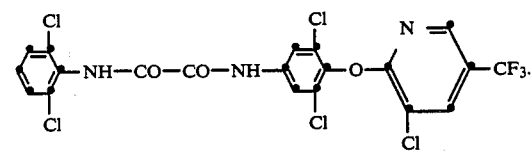

20. A compound according to claim 10 of the formula

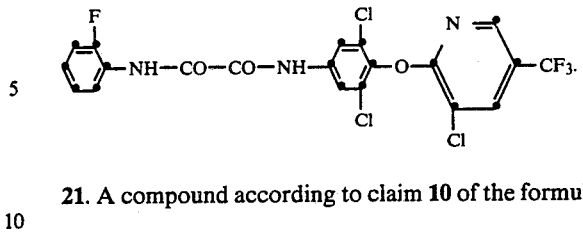

21. A compound according to claim 10 of the formula

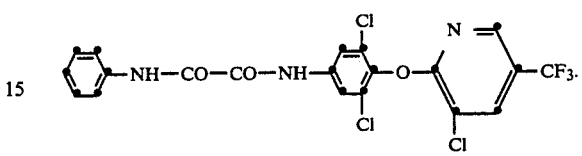

22. A pesticidal composition which comprises an effective amount of a compound of the formula

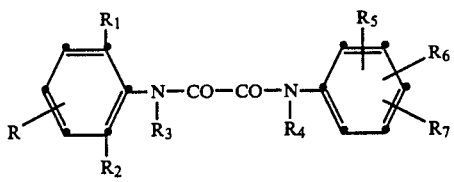

wherein
R is hydrogen, halogen, $C_1-C_4$alkyl, methoxy, ethoxy, $C_1-C_3$fluoroalkoxy containing 1 to 5 fluorine atoms,
$R_1$ is hydrogen, halogen, methyl, methoxy, ethoxy, $C_1-C_2$fluoroalkoxy containing 1 to 5 fluorine atoms, $C_1-C_3$alkylthio or cyano,
$R_2$ is hydrogen, halogen, methyl or methoxy,
$R_3$ and $R_4$ are each independently hydrogen or methyl,
$R_5$ is hydrogen, halogen, methyl, acetyl or trifluoromethyl,
$R_6$ is hydrogen, halogen, methyl, trifluoromethyl or carbalkoxy containing 1 to 4 carbon atoms in the alkyl moiety, and
$R_7$ is the

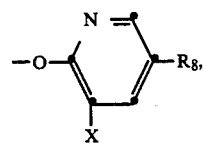

radical, in which $R_8$ is hydrogen, chlorine, trifluoromethyl or a perhalogenated ethyl radical and X is hydrogen or chlorine; or is the

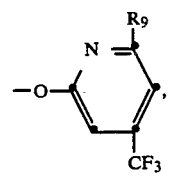

radical, in which $R_9$ is hydrogen, chlorine, bromine, methoxy or ethoxy, together with a suitable carrier.

23. A method of controlling insects, which comprises applying to said insects, or any of their various development stages, or their loci thereof, with a pesticidally effective amount of a compound of the formula

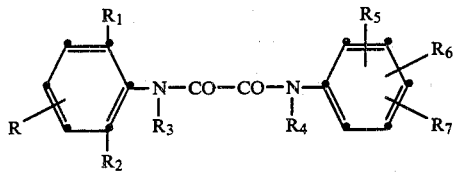

wherein
R is hydrogen, halogen, $C_1-C_4$alkyl, methoxy, ethoxy, $C_1-C_2$fluoroalkoxy containing 1 to 5 fluorine atoms,
$R_1$ is hydrogen, halogen, methyl, methoxy, ethoxy, $C_1-C_2$fluoroalkoxy containing 1 to 5 fluorine atoms, $C_1-C_3$alkylthio or cyano,
$R_2$ is hydrogen, halogen, methyl or methoxy,
$R_3$ and $R_4$ are each independently hydrogen or methyl,
$R_5$ is hydrogen, halogen, methyl, acetyl or trifluoromethyl,
$R_6$ is hydrogen, halogen, methyl, trifluoromethyl or carbalkoxy containing 1 to 4 carbon atoms in the alkyl moiety, and
$R_7$ is the

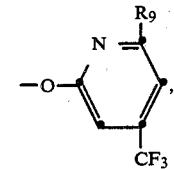

radical, in which $R_8$ is hydrogen, chlorine, trifluoromethyl or a perhalogenated ethyl radical and X is hydrogen or chlorine; or is the radical, in which $R_9$ is hydrogen, chlorine, bromine, methoxy or ethoxy.

24. The method of claim 23 wherein the pesticidally effective amount of the compound is applied to said insects at the larval stage or to their loci thereof.

* * * * *